US009551681B2

(12) United States Patent
Robitzki et al.

(10) Patent No.: US 9,551,681 B2
(45) Date of Patent: Jan. 24, 2017

(54) DEVICE AND METHOD FOR PARALLEL RECORDING OF IMPEDANCE SPECTRA AND FIELD POTENTIAL

(75) Inventors: Andrea Robitzki, Viernheim (DE); Heinz-Georg Jahnke, Leipzig (DE); Ronny Azendorf, Leipzig (DE)

(73) Assignee: Universitaet Leipzig, Leipzig (DE)

( * ) Notice: Subject to any disclaimer, the term of this patent is extended or adjusted under 35 U.S.C. 154(b) by 487 days.

(21) Appl. No.: 14/351,777

(22) PCT Filed: Aug. 13, 2012

(86) PCT No.: PCT/EP2012/065788
§ 371 (c)(1),
(2), (4) Date: Aug. 12, 2014

(87) PCT Pub. No.: WO2013/053513
PCT Pub. Date: Apr. 18, 2013

(65) Prior Publication Data
US 2014/0346058 A1 Nov. 27, 2014

(30) Foreign Application Priority Data

Oct. 14, 2011 (EP) .................................. 11185233

(51) Int. Cl.
*G01N 27/327* (2006.01)
*G01N 33/487* (2006.01)
*G01N 33/483* (2006.01)

(52) U.S. Cl.
CPC ........ *G01N 27/327* (2013.01); *G01N 33/4836* (2013.01); *G01N 33/48707* (2013.01); *G01N 33/48728* (2013.01)

(58) Field of Classification Search
CPC .............. G01N 27/327; G01N 33/4836; G01N 33/48707; G01N 33/48728
See application file for complete search history.

(56) References Cited

U.S. PATENT DOCUMENTS 5,981,268 A * 11/1999 Kovacs .................. C12M 41/46
324/447

FOREIGN PATENT DOCUMENTS

EP         2 103 933 A1      9/2009

OTHER PUBLICATIONS

Xiao L et al: "Evaluation of Doxorubicin Toxicity on Cardiomyocytes Using a Dual Functional Extracellular Biochip", Biosensors and Bioelectronics, E BV, NL, vol. 26, No. 4, Dec. 15, 2010, pp. 1493-1499, XP027546870, ISSN: 0956-5663.
Klosz D et al.: "Microcavity Array (MCA)-Based Biosensor Chip for Functional Drug Screening of 3D Tissue Models", Biosensors and Bioelectronics, Elsevier Bv, Nl vol. 23, No. 10, May 15, 2008 (May 15, 2008), pp. 1473-1480, XP022593616, ISSN: 0956-5663, DOI: 10.1016/J.BIOS.2008.01.003.
Wiegand Gerald et al.: "Fast Impedance Spectroscopy: General Aspects and Performance Study for Single Ion Channel Measurements," Review of Scientific Instruments, Aip, Melville, NY, US, vol. 71, No. 6, Jun. 1, 2000 (Jun. 1, 2000), pp. 2309-2320, XP012038328, ISSN: 0034-6748, 001: 10.1063/1.1150447.

* cited by examiner

*Primary Examiner* — Susan D Leong
(74) *Attorney, Agent, or Firm* — Polsinelli PC

(57) ABSTRACT

The present invention relates to a device and a method for parallel recording of impedance spectra and field potential of cells in vitro.

15 Claims, 13 Drawing Sheets c)

DEVICE AND METHOD FOR PARALLEL RECORDING OF IMPEDANCE SPECTRA AND FIELD POTENTIAL

The present invention relates to a device and a method for parallel recording of impedance spectra and field potential of cells in vitro.

Given the complex pathological mechanisms, drug development programs for neurodegenerative diseases such as Alzheimer's disease (AD), Parkinson's disease, Multiple Sclerosis (MS), bovine spongiform encephalopathy (BSE), Creutzfeldt Jacob disease (CJD), and various retinal degenerations predominantly depend mainly on whole animal models which are very expensive, laborious, and time consuming. Analyses of drug effects or pathological mechanisms are predominately performed by cell-destructive procedures like immunocytochemical, molecular biological, and/or proteinchemical methods.

Label-free detection and real-time monitoring of cellular alterations by the use of bioelectronic sensors and sensor-arrays is an emerging technology in the field of active pharmaceutical ingredients (API) development, drug safety testing as well as diagnostic purposes especially with regard to the field of personalized medicine. API development is an expensive and time consuming process that often ends up with high failure rates in clinical studies especially for complex and multifactorial diseases like neurodegenerative (e.g. Alzheimer's Disease) and cardiovascular diseases. So there is a bottleneck between initial compound screenings and (pre)clinical trials where there is a tremendous demand for cell/tissue based models that are capable of recapitulating complex diseases specific path mechanism and that are suitable for the use in high-throughput and high content screenings (HTS/HCT) to identify at early development stages the most suitable compound with regard to activity but also minimum unwanted side effects.

A main drawback of today's cell- and tissue based screening approaches is the use of classical end-point assays that are often limited in their read-out capabilities (target restriction etc.). To overcome these drawbacks there were strong efforts to establish label-free detection techniques for real-time monitoring of cellular alterations without influencing the cell. Two main bioelectronic techniques, the electrical impedance spectroscopy (EIS) and the electrophysiological recording (EPR) are promising for the use in screening platforms of pharmaceutical industry.

Impedance spectroscopy—also known as cellular dielectric spectroscopy (CDS) or electric impedance spectroscopy (EIS)—can be used to measure frequency dependent alterations of passive electrical properties of single cells by applying defined alternate currents and/or voltages. Since impedance spectroscopy is a non-invasive method, long-term measurements can be realized without influencing cellular behavior. Hence, the cellular read out reflects real time conditions without disturbing effects due to complex and long lasting physical procedures. This method is well suited to study a broad range of biological and medical problems. Impedance spectroscopy is discussed in further detail e.g. in EP 2 103 933 A1.

Electrophysiological recording (EPR) generally is a study of the electrical properties of biological cells and tissues. It involves measurement of voltage, voltage changes or electric current on a wide variety of scales from a single ion channel, whole cells to whole organs. It allows e.g. measurement of electric activity of neurons, in particular action potential activity. The extra cellular field potential is the electric potential produced by cells, e.g. nerve or muscle cells, outside the cell. These electric potentials are typically measured by extra cellular microelectrodes.

Despite outstanding advantages, the process of adaption or even replacement of existing screening techniques is a difficult process that could be mitigated by optimizing read out platforms to get the most possible comprehensive information from a single cell or tissue sample. So the combination of detection techniques like EIS and EPR could enormously increase the benefit for novel high content screening platforms. Moreover, integration of both technology platforms EIS and EPR in existing screening systems, mainly based on optical/fluorescence read-outs, could significantly improve API development platforms, and the informational output from a single cell/tissue sample could be further increased.

Beside API development, the combination and integration of EIS and EPR techniques represents a substantial improvement in risk assessment and drug safety testing. Since approval of novel therapeutics depends on more restrictive regulation policy (FDA, EMA) to minimize approval of therapeutics that show hazardous side effects when released to the market (e.g. cardiac arrhythmia) there are massive requirements to improve safety testing especially in the field of cardiotoxicity. These requirements lead to the development of e.g. automated patch clap platforms and to a boost for the development of microelectrode array based systems for EPR. In this area the combination of multiple label-free real-time monitoring techniques can improve safety of the tested API/compounds/chemicals by taking acquired data by different detection methods from the same sample to obtain a more comprehensive insight of toxic/side effects on electrogenic cells.

Impedance spectroscopy (EIS) and electrophysiological recording (EPR) are both suitable techniques for label-free detection and real-time monitoring of cellular alterations. There were various attempts to develop these basic methods further to systems/devices that are applicable for HTS/HCS platforms, especially with regard to ANSI-compatibility for titer plates in 96- and 384-well format, which is a prerequisite for automated screening platforms. EIS systems are described e.g. in WO2004/010103 A2, DE202005007547 U1 or WO2006/104839 A2. The disclosed systems are designed as multiwell arrays and capable for the use in standard 96 well ANSI format, and are partially commercial available. All these devices are described as two electrode configuration with optimization for impedance measurement, which means maximized electrode areas for lowering the self-impedance of the electrodes, mainly realized as interdigitated electrodes.

Several EPR multielectrode array systems and developments were described for electrogenic cells, which mean cardiomyocytes (e.g. in Rothermet et al., Cell PhysiolBiochem, 16: 51-58 (2005)) and neurons (e.g. in Berdichevsky et al., J Neurosci Methods 178(1): 59-64 (2009)). While EIS systems are mainly realized as two large area electrode systems, EPR systems typically require microelectrodes with a size near the cell-dimension for recording local field potentials with a high signal to noise ratio within a single culture unit. The systems are therefore typically designed as multielectrode arrays. The use of multielectrode arrays is preferable for cardiomyocytes to get information about excitation routing and retardation, and a prerequisite for monitoring spontaneous or stimulated neuronal network activity.

A high speed impedance analyzer is described in WO 2009/137440. The disclosed setup comprises large interdigitated electrodes for the EIS measurement used to study the short term effect of drugs on the beating frequency of cardiomyocytes. EPR measurement is not mentioned in this document. Thus, the data obtained by that system is not comparable to information that can be obtained from EPR signals with regard to local and time resolution (4 kHz for cardiomyocytes and up to typically 40 kHz for neurons). Only EPR signals provide information concerning the shape and the specific status of ion channels. Moreover this method is restricted to cardiomyocytes since the signal is recorded from large size interdigitated electrodes and therefore only an average signal over the whole culture in the chamber/well is obtained. This prohibits its use for neuron networks where high spatial resolution is required to record the local field potential of single active neurons.

For EPR measurements, microelectrodes with contact areas in the range of down to 1000 µm$^2$ are used instead of the large size interdigitated electrodes used for EIS. These typical EPR microelectrodes represent a challenge for EIS systems due to their high self-impedance, and require high precision impedance analyzers that offer high sensitivity to obtain suitable signals from the monitored cells and tissues. Due to these technical restrictions integration of both EPR and EIS into a single sensor array are up to nowonly realized by a separate set of electrodes for each detection method, in particular interdigitated electrodes for EIS and one or more microelectrodes for EPR.

Xiao et al. (Biosensors and Bioelectronics 26: 1493-1499, (2010)) evaluated doxorubicin toxicity on cardiomyocytes using a dual functional extracellular biochip. The biochip "Excell" as described in this document comprises both interdigitated electrodes for EIS and microelectrodes for EPR measurement. However as described in this document in the system for monitoring of extracellular field potential and cell-electrode impedance, the stimulus voltage necessary for impedance measurement caused electrical disturbance in the microelectrode area (MEA) measurement. Thus, the detection operation was conducted sequentially with rather long intermediate times (roughly one minute of a five minutes detection cycle) between impedance detection and MEA detection.

Thus, even separate electrodes and separate measurement circuits for EIS and EPR as suggested by Xiao et al. lead to interferences of the measurement prohibiting a parallel monitoring and making it necessary to use both methods with rather long intermediate times. Further, separate sets of electrodes mean that different areas of cells, cell clusters or tissue samples are investigated by the respective EPR and EIS measurement.

It would be desirable to suitably combine EPR and EIS into a single sensor array, such that both locally and timely synchronized measurement could be achieved. In particular, measurement of the same cell, cell cluster or tissue sample with both EPR and EIS would reveal more complete information on the status of the sample. A timely synchronized measurement would be desirable in order to obtain a fast update on the status of the sample after amendments of the environmental conditions, e.g. addition of a drug to the surrounding buffer solution.

Therefore, there is a need in the art to overcome the above mentioned problems and in particular to provide a device and a method for recording of both impedance spectra and EPR, in particular electric field potentials, both locally and timely synchronized.

The present invention relates to a system for monitoring impedance and electric potential of cells, in particular excitable cells such as cardiac cells or neuronal cells, in vitro, comprising a cell-substrate including at least one electrode for contacting said cells and at least one reference electrode, a device capable of impedance measurement between the electrodes (impedance analyzer), and a device for measuring the electric potential difference between the electrodes (potential analyzer). The system further comprises a switch for selectively connecting the electrodes either to the impedance analyzer or to the potential analyzer. It has been found that when a switch is used having low specific on-resistance, high off-isolation and high crosstalk isolation as specified in the claims, the same electrodes can be alternatingly connected either to the impedance analyzer or to the potential analyzer without causing the electrical disturbances which were observed in the art. Said system, which comprises an impedance analyzer and a potential analyzer, and in particular the switch as defined herein, which is able to connect the electrodes alternating between the analyzers, can excellently be used to record both impedance spectra and field potential of the cells to be investigated in vitro.

The system according to the present invention comprises a cell-substrate, typically comprising at least one recording chamber. The recording chamber typically contains the cells or the organotypic tissue which is subjected to both the impedance measurement and the electric potential measurement. The recording chambers furthermore contain at least one electrode for contacting the cells and at least one reference electrode.

During measurement, e.g. the impedance measurement, the reference electrode is typically in direct contact with the culture medium or possesses an additional layer which is in direct contact with the culture medium. The additional layer can be a polymer coating.

Preferably, the reference electrode is in direct contact with the culture medium. The electrodes can be made of any material having the necessary electric conductivity. Suitable materials for electrode based impedance measurement and electric potential measurement are known in the art. Preferably, the electrodes are made of gold, platinum, indium tinoxide ITO, silver, copper, iridium or alloys thereof. Depending on the used material, the thickness of the electrodes is preferably between 10 nm and 100 µm, further preferred between 50 nm and 10 µm, and most preferred between 100 nm and 1 µm. In order to provide higher sensitivity and higher signal to noise ratio with regard to the used cell type/cell culture model, the size of the electrode for contacting said cells is preferably at most 1 mm$^2$, more preferred at most 10,000 µm$^2$ and most preferred at most 500 µm$^2$. The size of the reference electrode should be several orders larger than the measurement electrode to minimize cellular signal contributions from cells adhered on the reference electrode. Therefore, the size of the reference electrode is typically larger than the size of the electrodes for contacting said cells, e.g. preferably 10 times larger, more preferably 100 times larger, in particular 1000 times larger. Preferably, the size of the reference electrode is at least 5,000 µm$^2$, more preferred at least 100,000 µm$^2$, and most preferred at least 1 mm$^2$, or above. Preferably, the size of the reference electrode is at most 50 mm$^2$, more preferred at most 10 mm$^2$, e.g. at most 5 mm$^2$ or at most 2 mm$^2$, or below.

The electrodes are typically attached to the bottom of the recording chambers, wherein the recording chambers are preferably defined by a multiwell plate or multiwell frame. The electrodes can be deposited on the bottom of the recording chambers by means of semiconductor technology. Electrodes can e.g. be spotted onto silicon oxide, polyethylene (PE), glass, or comparable substrates.

The reference electrode and the electrode for contacting the cells are electrically isolated from each other by suitable means as known in the art, e.g. a passivation layer or local separation.

The electrode for contacting the cells may be one ore more electrode(s), in particular a microelectrode array, beside the reference electrode on the bottom of the cell-substrate, i.e. the recording chambers. Alternatively, the electrode for contacting the cells may be an additional electrode having a stamp-like shape or a pin-like shape, which is preferably moveable in at least two directions so that it can be contacted with or removed from the cells, the organotypic tissue or the culture medium. Preferably at least one electrode for contacting said cells is a microelectrode, more preferably all electrodes contacting said cells are microelectrodes. Microelectrodes preferably have a size of at most 10,000 $\mu m^2$, more preferably at most 500 $\mu m^2$.

The preferred cell-substrate, i.e. the recording chambers according to the present invention, preferably comprises commercially available multiwell plates or bottomless multiwell frames. It is even further preferred to use standard footprint multiple plate formats according to the Society of biomolecular Screening (SBS). Preferably, the cell-substrate according to the present invention is based on a standard bottomless multiwell frame, i.e. a single 384 well plate comprising 384 recording chambers, a 192 plate comprising 192 recording chambers, etc. Depending on the used multi well format, a different number of microelectrodes can be integrated in the cell-substrate per well. Each recording chamber contains at least one reference electrode and at least one electrode for contacting said cells. Accordingly, each recording chamber comprises at least two electrodes with two electrodes per well being preferred, e.g. per well of 384 multi well plate 384×2 electrodes. In such a setup a multi well plate having 768 electrical connections can be prepared, which is still in accordance with ANSI requirements for multi well plates. The recording chamber can also contain two, four or eight microelectrodes, e.g. per well of a 96 multi well plate, or 16 microelectrodes per well of a 48 multiwell plate. The electrode array size can be adapted to the appropriate well size.

The cell-substrate in the system according to the present invention typically comprises a substrate on which the electrodes, connection pads etc. of the recording chamber can be deposited. The resulting substrate with electrodes, conductors and connection pads deposited thereon is typically in the form of a multiwell array. The substrate can be made of glass, quartz glass, borosilicate glass, silicon, ceramic, polymer, polymethylene, polypropylene, polystyrol, polyester, polycarbonate or any other materials suited for sputtering electrodes and conductors. The thickness of the substrate is typically in the range of about 100 $\mu m$ to several millimeters, e.g. 0.1 mm to 2 mm, and depends on the desired material used for its preparation. If glass is used as substrate the thickness can vary from less than a millimeter to several millimeters. In case the substrate is a polymer, it can be used as a thin foil of a few 100 $\mu m$ whereon electrodes can be deposited. The electrodes, conductors and connections/ground pads are preferably integrated in the bottom substrate. Additionally, the substrate can comprise a thin foil on its surface to protect the electrical setup.

The system according to the present invention comprises a commercial or custom made impedance analyzer system capable of impedance measurement with high time resolution preferably in the second range, more preferably in the millisecond range and most preferred in the microsecond range. The impedance analyzer is preferably suitable to measure impedance at low voltage levels of below 100 mV, more preferred below 15 mV and in particular below 10 mV. This ensures minimal influence on the sample. Furthermore the impedance analyzer should be suitable to perform the impedance measurement of these voltage levels on microelectrodes which exhibit a high self-impedance in the range of 100 kOhm to 1 MOhm, at 500 Hz with an accuracy of preferably at least 0.1% to assure a suitable signal to noise ratio. Such devices are known in the art. Suitable impedance analyzers are e.g. available from ScioSpec Scientific Instruments GmbH, e.g. ScioSpeclCX-5 or ScioSpec SCX-3. Further impedance analyzers with appropriate performance are e.g. Agilent 4294A (Agilent Technologies) and Solartron 1260A+1296A high impedance dielectric interface (Solartron Analytical). Typically, the impedance analyzer is connected to a data processing system, e.g. a personal computer system.

The system according to the present invention further comprises a device for measuring the electric potential difference between the electrodes, i.e. a potential analyzer with high time resolution, preferably in the second range, more preferably in the millisecond range and most preferred in the microsecond range. Suitable potential analyzers are e.g. high speed voltage meters, preferably multichannel voltage meters, which are typically based on an analog-digital converter (ADC). One ADC can be used for each channel, i.e. each electrode, preferably several channels are multiplexed to one ADC. Typical sampling rates for the ADC are, dependent on the number of channels per ADC, at least 1 MHz more preferably at least 2 MHz, even more preferably at least 10 MHz, in particular at least 100 MHz. Preferably the digitalization resolution is at least 12 bit, more preferably 14 bit, even more preferred 16 bit, in particular 24 bit. Suitable analog-digital converters are known in the art, and available e.g. by Analog Devices (AD 7667, AD 7626, AD 9446) or Texas Instruments (AD 5482).

In a preferred embodiment the system according to the present invention additionally comprises a multiplexer, which is preferably connected to the impedance analyzer. The multiplexer is a device that performs multiplexing. Multiplexing means connecting two or more electrodes for contacting said cells to one impedance analyzer, such that not for each electrode for contacting said cell, e.g. each well, an impedance analyzer is necessary. Using a multiplexer is typically appropriate when several electrodes for contacting said cells are to be measured in parallel, e.g. each electrode of a 96 multi well plate, 192 multi well plate or 384 multi well plate. The multiplexer is typically based on time-division multiplexing, i.e. connecting the impedance analyzer to one electrode for contacting said cells after the other. As the multiplexer is an electronic circuit element positioned in the measurement pathway of the impedance analyzer, preferably the multiplexer provides a low signal alteration (distortion) as far as possible. In particular, in the voltage range below 100 mV, in particular below 15 mV, e.g. below 10 mV, the signal of the electrodes with a self-impedance in the range of at least 1 kOhm to 10 MOhm at 500 Hz, more preferably in the range of 100 kOhm to 1 MOhm at 500 Hz, and current flows in the range of $10^{-7}$ to $10^{-10}$ amperes should be multiplexed. The multiplexer preferably has an on-resistance lower than 10 Ohm, more preferably lower than 2 Ohm, in particular lower 0.5 Ohm. Preferably, the off-isolation is lower than −60 dB, preferably lower than −75 dB, in particular lower than −90 dB. Preferably, the crosstalk (channel-two-channel) is lower than −60 dB, more preferably −75 dB, in particular lower than −90 dB. Further, the multiplexer should provide fast switching capabilities, preferably in the microsecond time range. Preferably, the switching times should be below 100 ns in particular below 50 ns. Suitable devices are e.g. the ADG731 or ADG725 from Analog Devices, USA.

In order to provide a suitable environment for the cells through screening, especially for testing compounds (drug or toxic components) to the cells, the system according to the present application may further comprise an automated liquid handling system that also provides a humidified atmosphere (e.g. 37° C., 5% $CO_2$, 95% air). Suitable liquid handling and robotic systems are e.g. Freedom EVO®, TECAN Trading AG (Switzerland); Biomek FX systems, Biomek® Assay Workstation, Beckmann Coulter, or Biorobot 8000, Qiagen.

The system according to the present invention further comprises a switch for selectively connecting the electrodes either to the impedance analyzer or to the potential analyzer. Said switch must be suitable to connect the counter electrode and the electrode(s) for contacting said cells in a first switching state to the impedance analyzer. This means that the counter electrode is connected to the counter electrode input of the impedance analyzer and at least one electrode for contacting said cells is connected, preferably via a multiplexer, to the input of the impedance analyzer. Preferably all electrodes for contacting said cells are connected, more preferably via a multiplexer, to the input(s) of the impedance analyzer. In this position of the switch, the impedance measurement can be conducted by the impedance analyzer. The switch is capable of switching the electrodes in a second switching state to the potential analyzer, i.e. switching the counter electrode to ground and at least one, preferably all, electrodes for contacting said cells to the potential analyzer input, preferably via a pre-amplification device. In this second switching state the potential analyzer can measure the electric potential difference between the reference electrode and at least one electrode for contacting said cells. Since the extracellular field potentials are typically in the microvolt range, preferably low noise amplifiers are used for pre-amplification. Preferably, the noise level of the amplifier (pre-amplifier) is lower than 25 nV/√Hz, more preferably lower than 10 nV/√Hz, in particular lower than 5 nV/√Hz. The noise level is defined as known in the art. Preferably, the common mode input range values of the amplifier is at least $10^7$ Ohm, more preferably $10^{10}$ Ohm, in particular $10^{12}$ Ohm. Suitable operation and/or instrumentation amplifiers for the pre-amplification devices are known in the art, e.g. OPV from Texas Instruments TLC 2274 or OPV from Analog Devices OPA 4228.

The switch of the system according to the present invention is capable of switching the electrodes between the analyzers, i.e. the impedance analyzer and the potential analyzer, preferably with low switching noise. The switch used in the system according to the present invention has an on-resistance lower than 50 Ohm. On-resistance corresponds to the electrical resistance of the switch in "on state", i.e. of a closed switch. Wishing not to be bound by theory it is assumed that the low switch on-resistance is critically in order to reduce the influence on the impedance measurement signals, and to allow suitable impedance measurement with the electrodes for contacting said cells, which electrodes are also suitable for EPR measurement. Preferably, the on-resistance is lower than 10 Ohm, more preferably below 5 Ohm, in particular lower than 2 Ohm. The on-resistance ($R_{ON}$) as used herein is as known in the art a measure of the ohmic resistance of the switch in closed state and can be determined as shown in FIG. 7. $R_{ON}$ is typically measured at a current $I_{OS}$ of 10 mA at 25° C.

Further, the switch of the system according to the present application (switching component), in combination with the low on-resistance, has to provide a high off-isolation as well as high crosstalk (channel-to-channel) isolation. This assures that minimal signal alteration is caused by the switching component. The off-isolation, as well as the crosstalk isolation of the switch of the system according to the present application (switching component) are typically lower than −60 dB, preferably lower than −75 dB, in particular lower than −90 dB. Off-isolation as used herein is known in the art as a measurement of unwanted signal coupling through a switch in open (OFF) state. Off-isolation can be determined as shown in FIG. 8 according to: off-isolation (dB)=20 $\log(V_s/V_{OUT})$, typically measured at a signal frequency of 10 MHz at 25° C.

Crosstalk isolation as used herein is known in the art as a measurement of unwanted signal that is coupled through from one channel to another as a result of parasitic capacitance. Crosstalk isolation can be determined as shown in FIG. 9 according to: crosstalk isolation (dB)=20 $\log(V_s/V_{OUT})$, typically measured at a signal frequency of 10 MHz at 25° C.

Preferably, the switching component provides a low distortion of equal to or lower than 2%, preferably equal to or lower than 0.5%, in particular equal to or lower than 0.1%. Distortion (of a signal) as used herein is as known in the art the distortion of the output signal. It can be determined as the difference between maximum and minimum value of on-resistance relative to the on-resistance e.g. measured are the specified analog signal range. Preferably, the switch is capable of switching the electrode with high time resolution, i.e. short switching time ($t_{ON}$ and $t_{OFF}$) preferably in the millisecond range, e.g. a time range below 1000 microseconds, more preferably in the microsecond time range. Herein microsecond time range (resolution) means, that the time range for switching the electrodes is preferably below 1000 microseconds, more preferably below 100 microseconds, even more preferred below 10 microsecond, in particular below 2 microseconds, e.g. below 0.5 microseconds. Switching times as used herein are as known in the art and can be determined as shown in FIG. 10 (switching times $t_{ON}$ and $t_{OFF}$).

Preferably, the switch of the system according to the present application has a break-before-make time delay of at least 1 ns, more preferably in the range of 1 ns to 10 ns. Break-before-make time delay ($t_D$) is as known in the art and can be determined as shown in FIG. 11.

Preferably, the switch is capable of switching the electrodes between the analyzers with a frequency of at least 20 kHz, more preferably at least 50 kHz, in particular at least 100 kHz. Suitable ultra fast switching devices are known in the art, e.g. MAXIM 4619, ADG 774 or ADG 794. Further suitable devices allowing fast switchingdata pathway routing and measurement control of measurement pathways for hundreds of electrodes/channels in the (sub) microsecond time scale are e.g. ATXMEGA of (Atmel), Cyclone/Aria of (Alterra) and Spartan (Xilinx). Preferably, the switch is based on, in particular integrated in, a digital signal processor (DSP) or a field programmable gate array (FPGA) as known in the art. These devices are known as programmable, highly parallel devices based on integrated circuits which can be easily configured for the desired application, and can readily be updated in functionality, while having rather low non-recurring engineering costs. By using such devices, high switching frequencies and low switching times for many parallel contacts can be achieved. Suitable devices for controlling the signal processing can e.g. be based on ASIC or Fusion-Mixed-Signal-FPGAs (Microsemi).

All electrical parameters of the switch and the further devices are determined at 25° C., unless otherwise stated.

The present invention further relates to a method for monitoring impedance and electric potential of cells, preferably excitable cells, in particular cardiac cells or neuronal cells, comprising the step of providing a system as described above, and measuring the impedance and the electric potentials of the cells. The electrodes are switched between the analyzers, i.e. the impedance analyzer and the potential analyzer, by a switch as defined above.

In the method of the present invention preferably both the impedance analyzer and the potential analyzer have a low, more preferably a millisecond time resolution. In such a setup, the electrodes are preferably switched between the analyzers in a time range below 1000 microseconds, preferably below 10 microseconds, in particular below 2 microseconds, e.g. below 0.5 microseconds. Preferably, the frequency of switching is as described above.

In a particular preferred embodiment, the system of the present invention is capable of, and the method according to the present invention comprises switching the electrodes such that the impedance is measured between two sampling points of the electric potential measurement (EPR). EPR measurement is typically conducted at a specific sampling rate, e.g. 1 kHz to 1 MHz, preferably 2 kHz to 100 MHz, in particular 4 kHz to 100 kHz sampling rate. Further, typically a multiplexer (MUX) is used together with the voltage meter, typically an analog-digital converter (ADC). Thus, there is an interval between two sampling points, dependent on the sampling rate and sampling duration. Preferably this interval is used for EIS measurement. E.g. when the typical circuit design comprises a 16 channel MUX within at least 10 MHz ADC and a sampling frequency of 4 kHz, there is a time interval between two samples of about 250 microseconds. Due to the multiplexing of the 16 channels there is a digitalization window of roughly 25 microseconds per channel, which means there is a time domain of more than 200 microseconds that can be used for EIS. Correspondingly, a sampling rate of 20 kHz leads to a time interval of 50 microseconds between the sampling point, and thus roughly 30 microseconds time interval which can be used for EIS. Thus, with the system according to the present invention, in particular when the switch is capable of switching the electrodes between the analyzer with microsecond time resolution, in particular in the range below 5, further preferred below 2 microseconds, EIS measurement can be conducted between two sampling points of the EPR measurement. This results in a gapless EPR data stream. The acquired discrete impedance values for this frequencies or even impedance spectra can be recorded, only limited by the EPR sampling frequency. Such setup provides excellent, gapless and nearly simultaneously measurement of both EPR and EIS.

In the system and in the method according to the present invention, preferably at least one electrode is a microelectrode, and the cell-substrate is preferably a microelectrode array, as known in the art.

The invention will be further illustrated with reference to the enclosed figures. These examples are not intended to limit the scope of the invention.

In the present application both techniques of impedance spectroscopy (EIS) and electrophysiological recording (EPR) are combined in one system. Thereby, a high throughput screening/high content screening (HTS/HCS) system is provided, which is preferably and advantageously based on compatible ANSI 96 or ANSI 384 multiwell titer plates. Both impedance spectroscopy and electrophysiological recording use the same microelectrodes, i.e. both analyzers are connected to the same electrodes, i.e. at least one reference electrode (also designated as ground-/or counter-electrode) and the electrode for contacting that cells (also designated as working-electrode). Thereby, the connections are reduced to a minimum. Moreover, the recording from the same electrode offers the direct correlation of the localized EIS data with the field potential data obtained from the same cell/cell cluster. If more electrodes, e.g. of a micro array, are present in one recording chamber, at least one of the several electrodes used for EPR is used for EIS.

Figure 1:
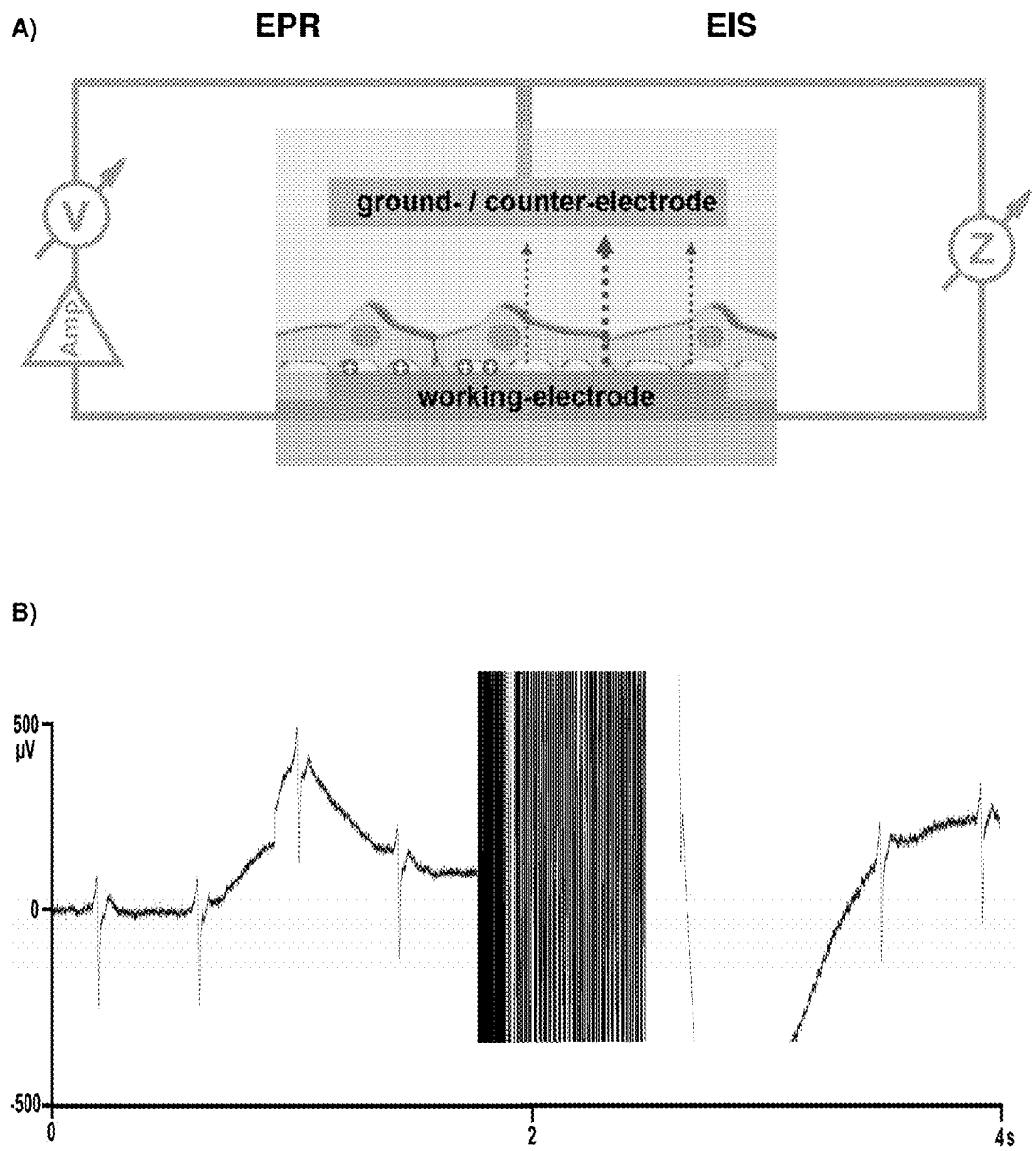
FIG. 1 shows interference caused by connection of electrophysiological recording (EPR) and electrochemical impedance spectroscopy (EIS) measurement circuit path to the same microelectrode as known in the art.
Figure 1:
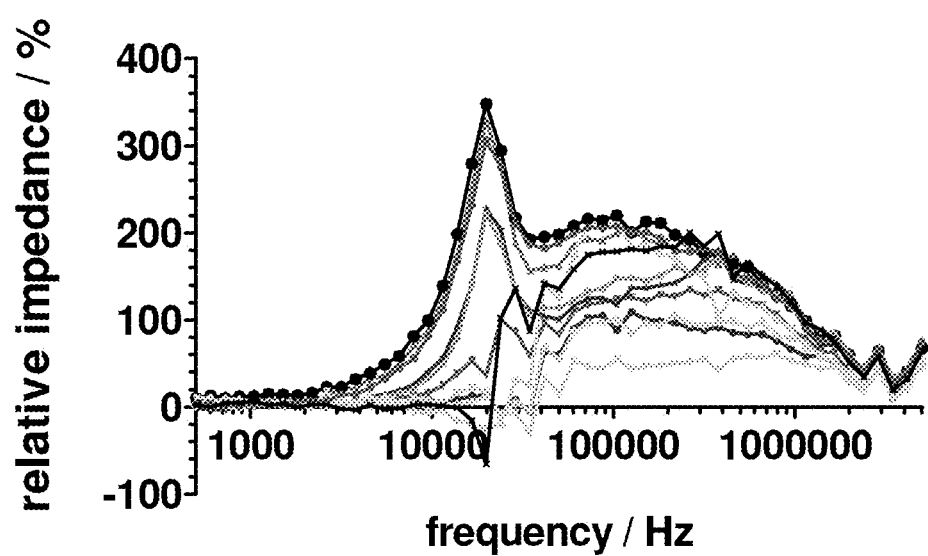

One preferred embodiment of the system according to the present invention is indicated in FIG. 1. The working electrode and the reference electrode are used both for EPR, which is a passive detection method mainly comprising an amplification device and a voltage meter. The same electrodes are used for impedance spectroscopy, which is an active detection method wherein an alternating current voltage is applied to the electrodes. In order not to influence the cells/cell clusters that have to be monitored, the injected charge has to be limited to the mV range, preferably below 100 mV, more preferably below 10 mV depending on the used microelectrodes size.

As indicated in FIG. 1, due to the opposite nature of EPR and EIS, measurement of both data at the same time is not possible. Rather the measurement circuit paths cause interference and disturbance to each other when connected and operated at the same time (in this case a circular gold microelectrode with 200 μm diameter was applied). Even in the case that no active measurement of the other method is carried out, only the connection of the circuit paths may induce unacceptable interference to the EPR amplifier circuits (cf. FIG. 1B) and vice versa an inactive EPR circuit path may cause disturbances in the cell cultures specific impedance measurement (cf. FIG. 1 C).

In detail, when EPR streams are acquired and EIS measurement is started in the same culture chamber or at least in compartments that are electrically connected, the injected alternating current (typically with potentials in the mV range) leads to disturbance while current is applied (FIG. 1, B at 1.9 to 2.3 seconds), but also after EIS recording and even before. In general, the EIS measurement leads to an EPR disturbance in the time range of several seconds independent from the time window that is needed for the EIS acquisition. As it can be seen from the EIS data that can be acquired parallel to EPR measurement, they are also significant artifacts introduced by the connected EPR circuit path, even when EPR recording is not active (FIG. 1, C). This disturbance may be caused by the high self-impedance of microelectrodes in the aqueous environment of cell-compatible media and buffer solutions together with the unshielded connection to further electrical devices of the respective other detection method.

With regard to the high self-impedance of the microelectrodes with typically $10^5$ to $10^6$ Ohms at 100 Hz, there are high demands on the impedance analyzer for measurement of currents in the nA or even pA range. This may be the reason for the high sensitivity of EIS circuit paths to other connected electronic elements like EPR circuits, in particular if these are not shielded or grounded.

To prevent these interferences between EPR and EIS measurements, in the present application a switch as defined above selectively connects the electrodes either to the impedance analyzer or to the potential analyzer. Preferably, the input of the corresponding impedance analyzer or potential analyzer not in useis grounded, when the respective other analyzer is connected to the electrodes. Thereby, the sensitive amplifiers are protected from charging or voltage pulses which may occur when the electrodes are switched or not connected.

Figure 2:
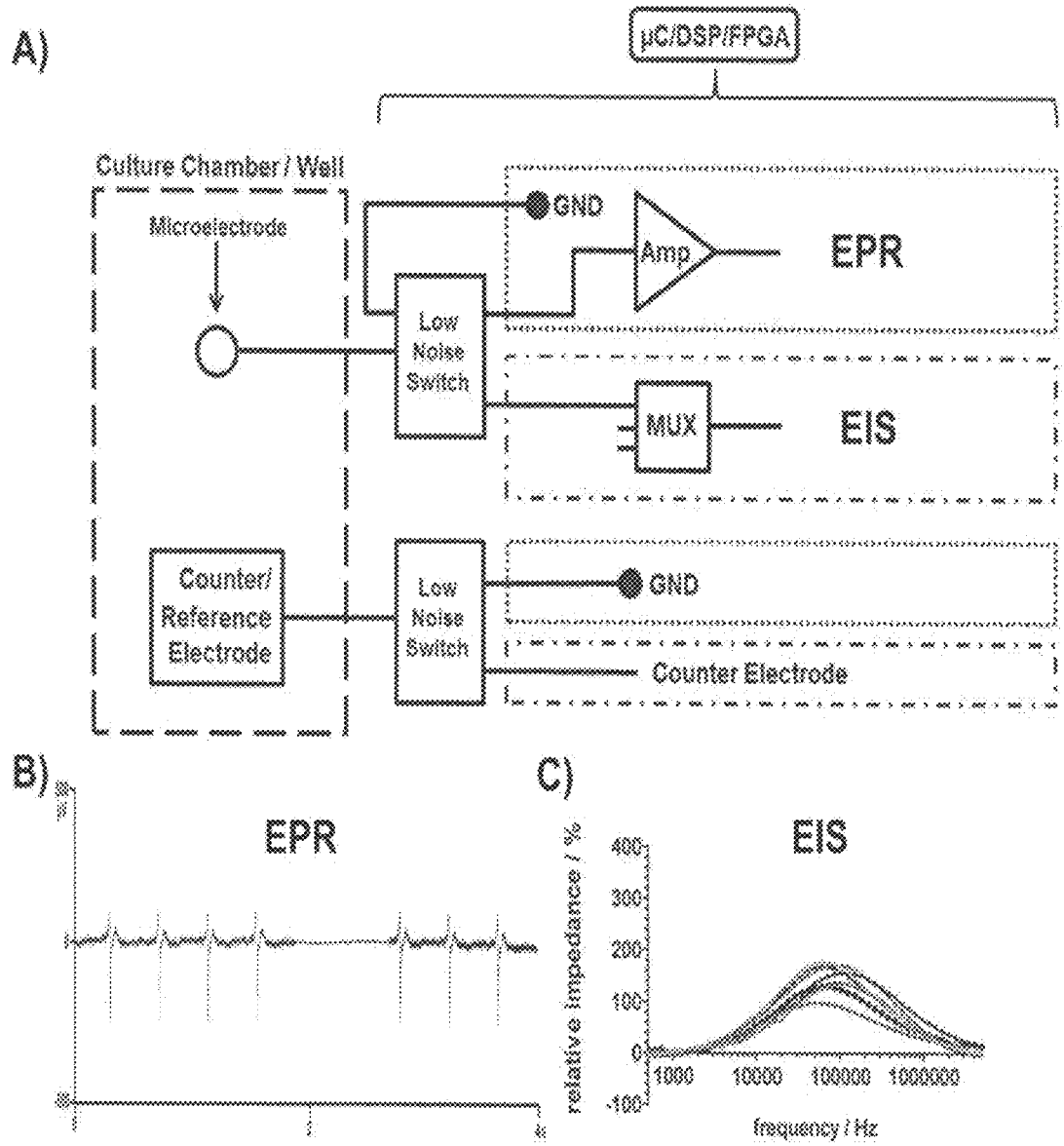
FIG. 2 shows a circuit design for elimination of measurement artifacts.

In a preferred embodiment the switch used in the system according to the present invention based on and is in particular integrated in a DSP/FPGA (digital signal processor and/or field programmable gate array) switch, which is more preferred combined with a high capacity (μC) element or a similar device as known in the art to reduce the switching noise (cf. FIG. 2). This low noise switch assures disturbance free operation of both measurements by connecting both the reference electrodes and the electrodes for contacting said cells to the respective analyzer, and preferably connecting the inputs of the other analyzer to ground. E.g. when the measurement electrode is switched to the EIS circuit path, the reference electrode is switched to the counter electrode connection of the impedance analyzer. In order to avoid EPR amplify overcharge, the amplifier input is switched to the ground. The opposite case, when the measurement electrode is switched to the EPR circuit path, the reference electrode is switched to the ground. The high-capacity μC which assures low noise switching, and/or the appropriate DSP/FPGA assures synchronous switching of all paths in the low second, preferably millisecond, in particular microsecond range. In order to avoid overcharge of the EPR amplifier circuits, the amplifier inputs have to be connected to the ground just right before the reference electrode is connected to the counter electrode connection of the impedance analyzer. This assures that the EPR stream is interrupted while the impedance spectrum, which needs application of an alternating current voltage, is recorded. During interruption of the EPR stream, a gap in the data is created, which is filled by a zero field potential due to the connection to the ground without any disturbance by other circuits (FIG. 2, B). The corresponding impedance data recorded during interruption of the EPR stream is free of disturbances caused by interference of the EPR circuits (FIG. 2, C).

Depending on the used high precision impedance analyzer as well as on the measurement parameters, the impedance spectrum acquisition causes an EPR stream gap (zero field potential). Due to the fact that this gap is caused and controlled by the switch as described above, a time stamp data can be transferred to the electronic data processing, typically a computer work station, and may be used for the data analyses, where the gaps are typically eliminated e.g. for the frequency analyses. Thus, while using the switch as described above for the synchronized switching of electrodes on low time scales the measurement artifacts as shown in FIG. 1 can be eliminated for both methods (cf. FIGS. 2, B and C).

Figure 3:
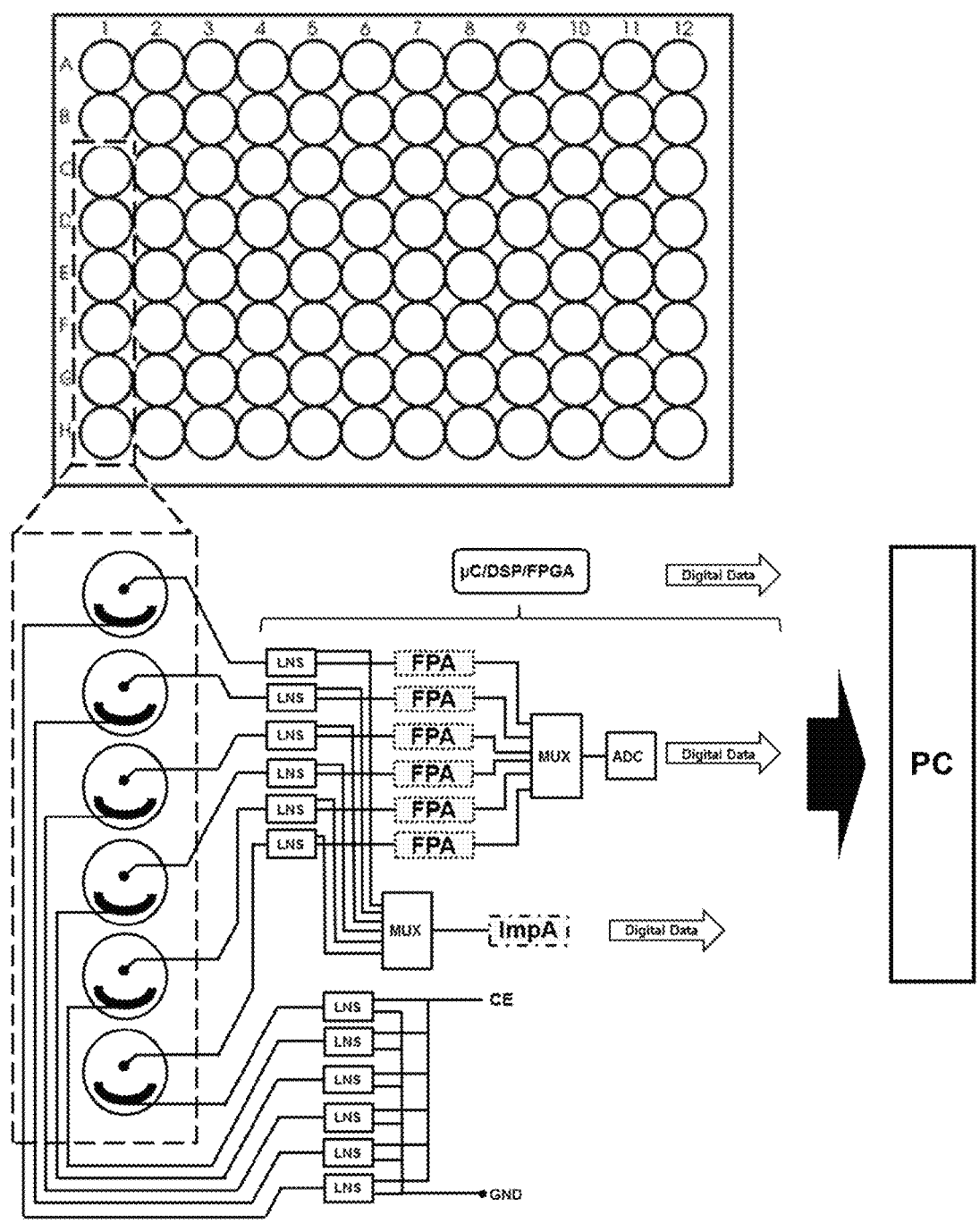
FIG. 3 shows the use of a system according to the present invention in multiwell arrays.

An experimental setup for using both EPR and EIS on the same electrodes, which is based on the preferred 96-multi-well array, is shown in FIG. 3. An array is used with at least one measurement electrode and one reference electrode for each well of the 96-well plate as indicated in said figure. Each of the measurement electrodes as well as each reference electrode is connected to a low noise switch (LNS) that is connected both to the EPR and EIS measurement path. The EPR path consists of field potential amplifier (FPA) circuits that are typically amplifying the cellular potential in the micro volt range by a suitable factor, e.g. 700 to 1200, and eliminate noise around the cellular signal frequency range. Afterwards the FPA paths are multiplexed (MUX) and digitized by an analog-digital-converter (ADC). For the EPR-path the reference electrodes (CE) are switched to the ground and for the EIS-path to the counter electrode connection of the impedance analyzer (ImpA). The data is collected and analyzed in a personal computer (PC).

The MUX is typically positioned after the FPA paths as this further reduces crosstalk and noise compared to positioning the MUX in front of the FPA. Preferably there is one FPA circuit for each electrode. Depending on the used MUX and ADC as well as the maximum sampling frequency that has to be achieved, typically 30-60 channels are multiplexed per ADC.

The EIS measurement path consists of a low noise multiplexer which is connected to a high procession impedance analyzer (ImpA). The ImpA should be capable to measure the impedance spectrum on multi electrodes with high self-impedance ($10^5$ to $10^6$ Ohm at 100 Hz) at low voltage amplitudes (preferably below 100 mV, in particular below 10 mV) in an appropriate time range, preferably millisecond time range, more preferably microsecond time range. Impedance analyzers with appropriate performance are e.g. Agilent 4294 A (Agilent Technologies) and Solartron 1260A+1296A high impedance dielectric interface (Solartron Analytical), as well as appropriate analyzes like the ScioSpec ISX-03.

For the synchronous switching of all components a performance high capacity based-DSP/FPGAis used. With such a system the switching of the paths of both measurements can be controlled tightly and switching information (time stamps) can be added for the data analysis on the personal computer.

Figure 4:
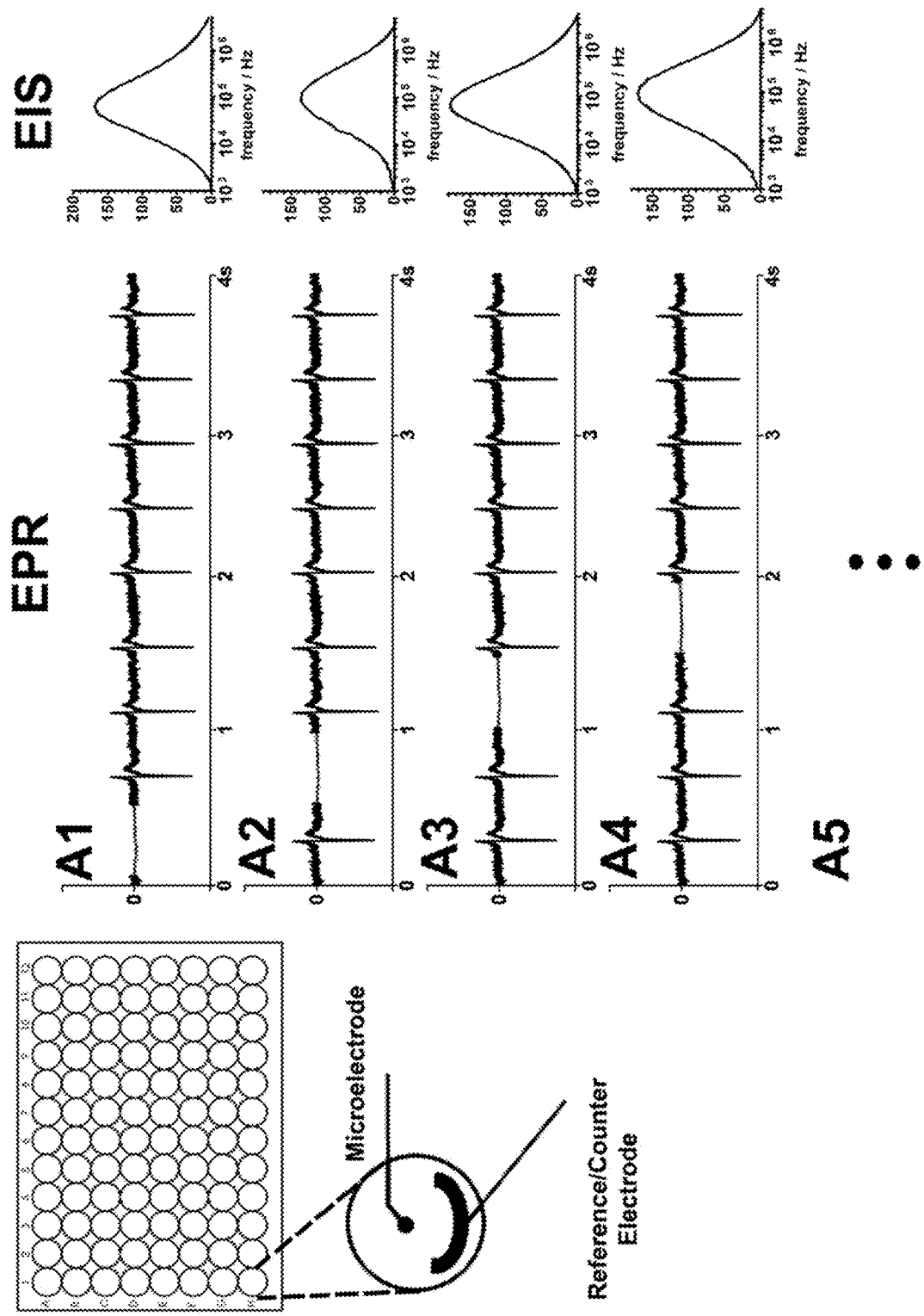
FIG. 4 shows the data acquisition by use of a system according to the present invention in multiwell arrays.

As shown in FIG. 4, EPR streams can continuously be recorded on all 96 electrodes while for the acquisition of EIS spectra the EPS stream of each well is synchronously interrupted by the low noise switch. The time for the acquisition of the impedance spectra depends on the used impedance analyzer as well as the acquisition parameter (frequency range, number of frequency points, averaging or integration time per acquired frequency, etc.). For example, when a ScioSpec ISX-3 is used with 51 frequency points equidistantly distributed between 1 kHz to 5 MHz, the acquisition time is 500 milliseconds. During this time window, the EPS stream is interrupted. To read-out all 96 wells, the switching and the impedance spectra acquisition is done sequentially. So the whole 96-well plate is read-out in less than one minute. The gap position data (obtained from the low noise switch) as well as the impedance spectra are analyzed by the analysis software where the cellular contribution (relative impedance) for each electrode/well is calculated (FIG. 4 right). The EPR streams are analyzed while cutting out the gaps, e.g. to obtain the frequency in contraction per minute and averaged signal shape (per minute).

To increase the obtained information per well, at least two measurement microelectrodes can be integrated per well. With an increase of measurement electrodes per well, preferably 2, 4, 8 electrodes for contacting said cell per well more preferred 2 or 4, in particular 4 electrodes, and one reference electrode per well, more data points can be obtained which can be averaged. On the other hand the electrode arrays in each well can be used for a spatiotemporal analysis, e.g. the excitation spreading of cardiomyocytes cultures (EPR) or the activity pattern of neuronal networks culture on the microelectrode array (EPR). In the same way impedance spectra can be assembled to a 2D impedance map.

Figure 5:
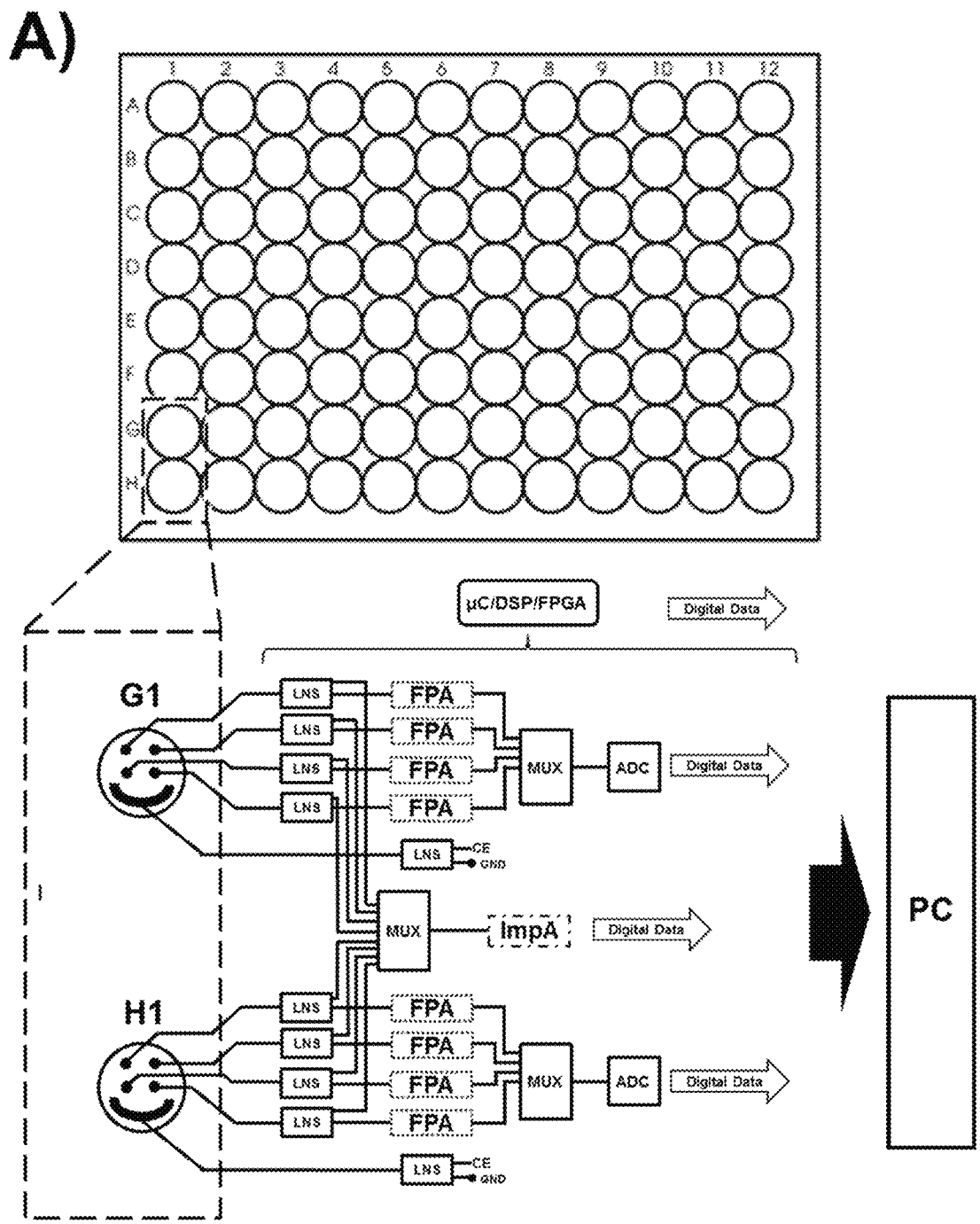
FIG. 5 shows the use of a system according to the present invention in multi electrode-multiwell arrays.
Figure 5:
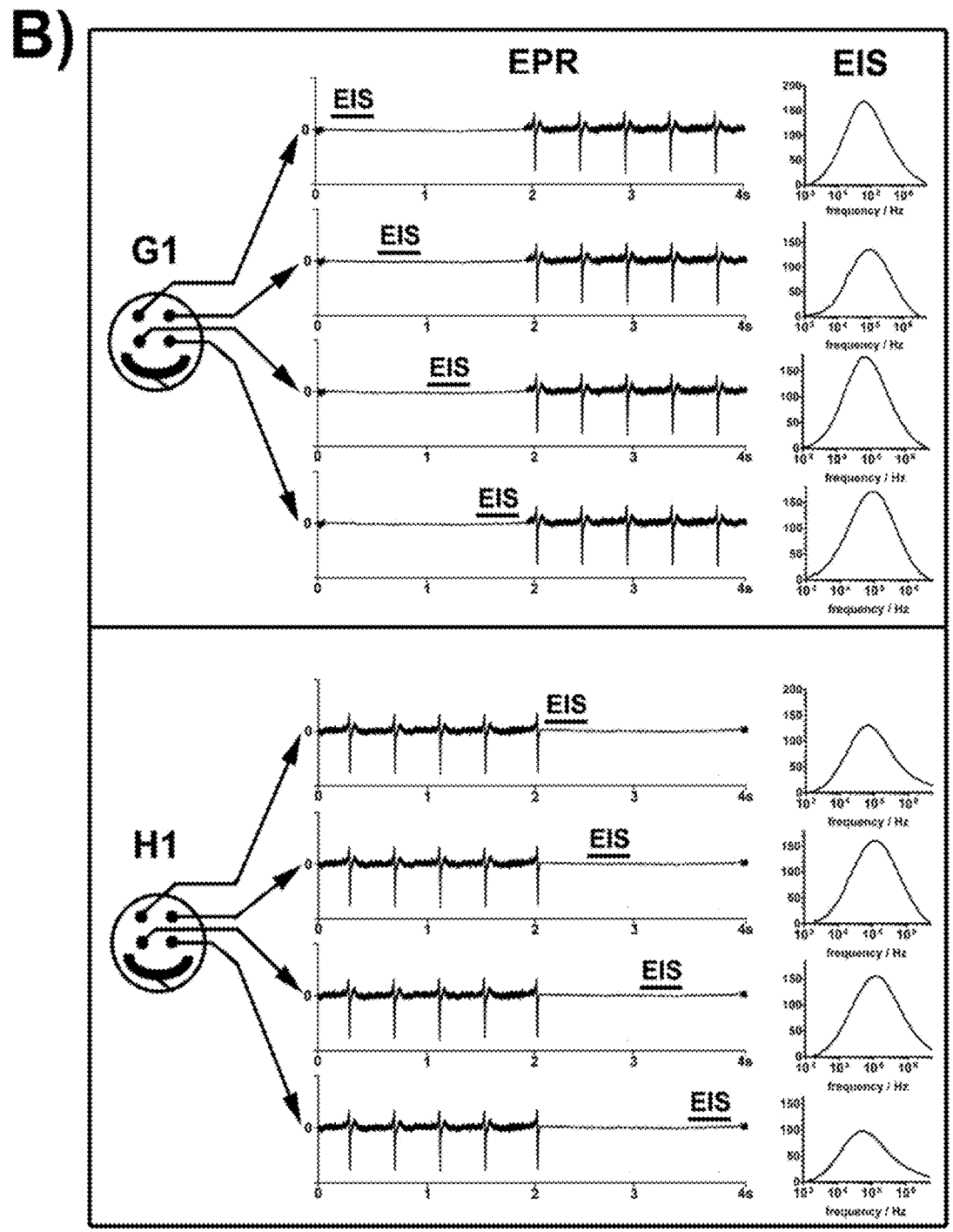

FIG. 5 shows an application where a 96-well plate comprises wells with four measurement electrodes and one counter/reference electrode per well. In this case there are 96×4 measurement electrodes with the same number of low noise switches (LNS) and field potential amplifier (FPR) paths that are connected to a multiplexer with typically 30 to 60 channels. The multiplexed EPR stream is digitized by an analog-digital-converter (ADC). All impedance related paths are multiplexed to an appropriate high precision impedance analyzer (ImpA) (cf. FIG. 5 A). Due to the fact that there are more than one measurement electrodes per well and congruent impedimetric measurement in the same well is technically not possible there exists an increased gap in the EPR streams per well (FIG. 5 B). This gap depends on the measurement time for one impedance spectrum and the number of measurement electrodes per well. E.g., an impedance spectrum from 1 kHz to 5 MHz is acquired in 500 milliseconds. This means that there is an EPR stream gap per well of two seconds. When using one precision impedance analyzer channel at the acquisition parameters as described above, the read-out of the whole plate needs roughly 200 seconds for whole impedance spectrum and EPR streams. From taking the data of the low noise switch into account during data analysis, the average frequency and signal shape parameters, e.g. per minute, can be calculated. To minimize the EPR stream gaps, impedance spectra parameters could be restricted to higher frequencies with less acquisition frequency. It is even possible to minimize the impedance spectrum to at least one discrete frequency, e.g. 100 kHz, where the impedance is determined. This way, the acquisition time can be reduced, e.g. to 25 microseconds when a high precision impedance analyzer like the ScioSpec SCX-3 is used.

To further reduce the measurement time of the whole plate, e.g. the 96-well plate, parallel channel high precision impedance analyzers (multichannel impedance analyzers), like FPGA-based measurement systems, can be used. With at least two or more parallel impedance acquisition channels, the acquisition time can be further reduced.

With the increase of measurement electrodes per well, the EPS stream gaps per well are extended. E.g. the use of 60 measurement electrodes per well would need 30 seconds for the former described whole spectrum acquisition, and with at least one impedance measurement channel there would be at least 50 minutes of acquisition time for the whole 96-well plate. The use of single frequency measurement and parallel impedance channel acquisition would reduce this to less than 5 seconds, but the acquired impedance data is considerably restricted. To avoid this restriction, and in particular to eliminate the EPR stream gap, the system according to the present application can be used to integrate the impedance spectrum acquisition directly without any gaps into the EPR stream acquisition as shown in FIG. 6.

Figure 6:
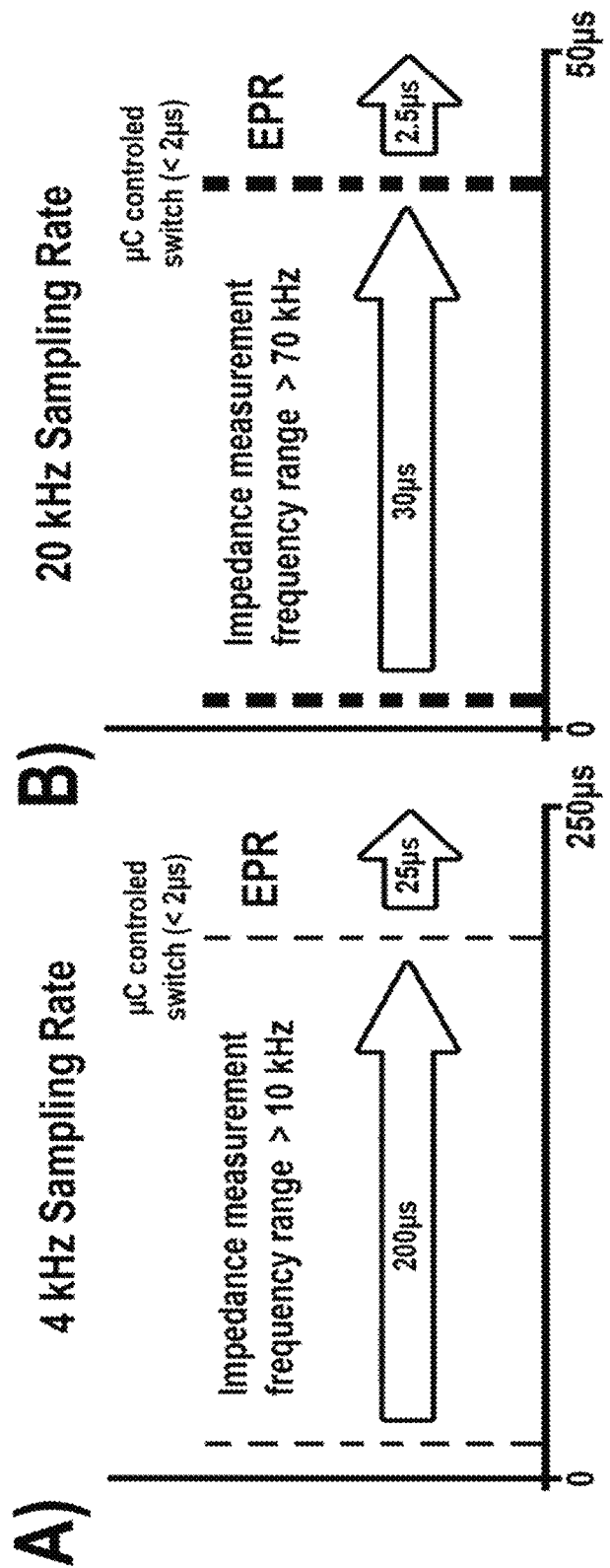
FIG. 6 shows the use of a system according to the present invention in a high speed DSP/FPGA control set-up for gapless parallel recording.
Figure 6:
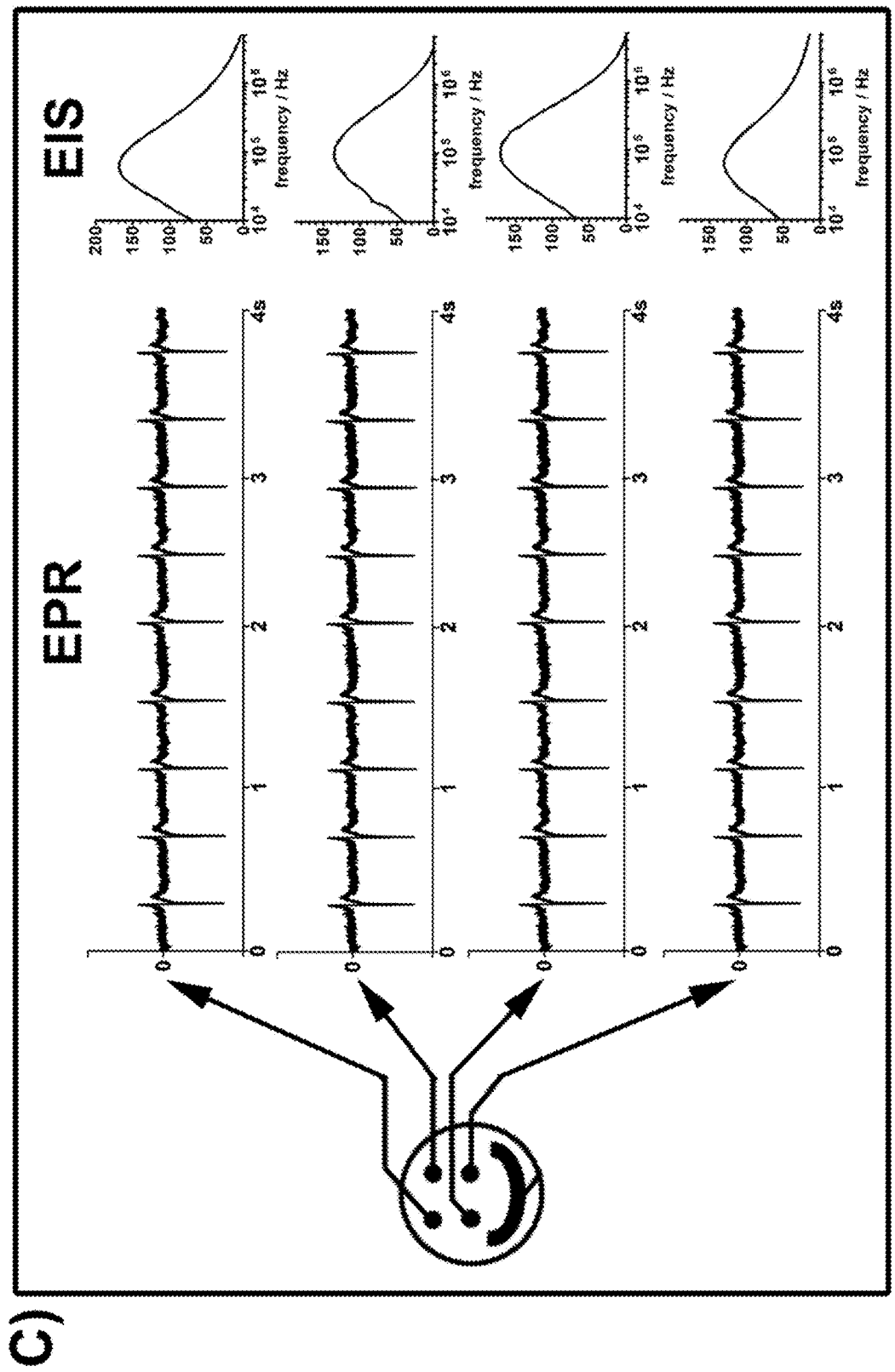
Figure 7:
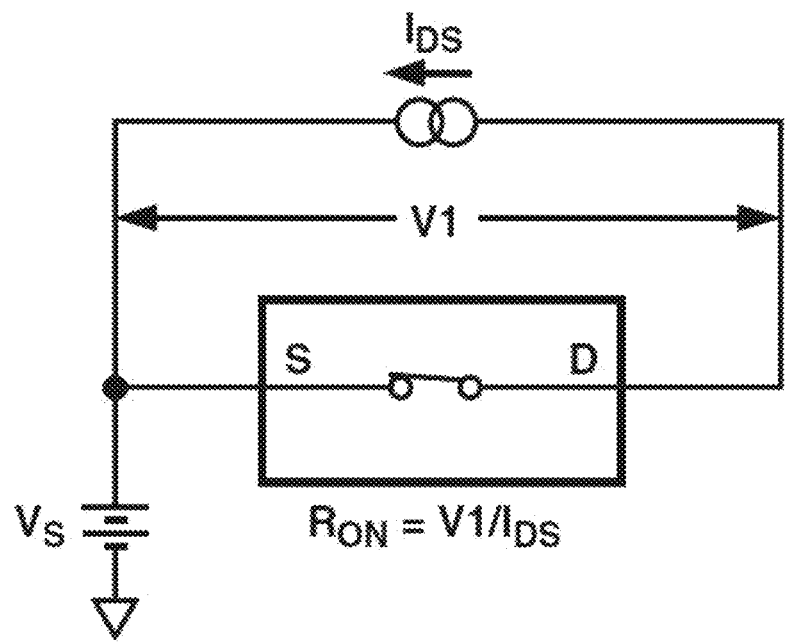
FIG. 7 shows the test circuit for determination of on-resistance.
Figure 8:
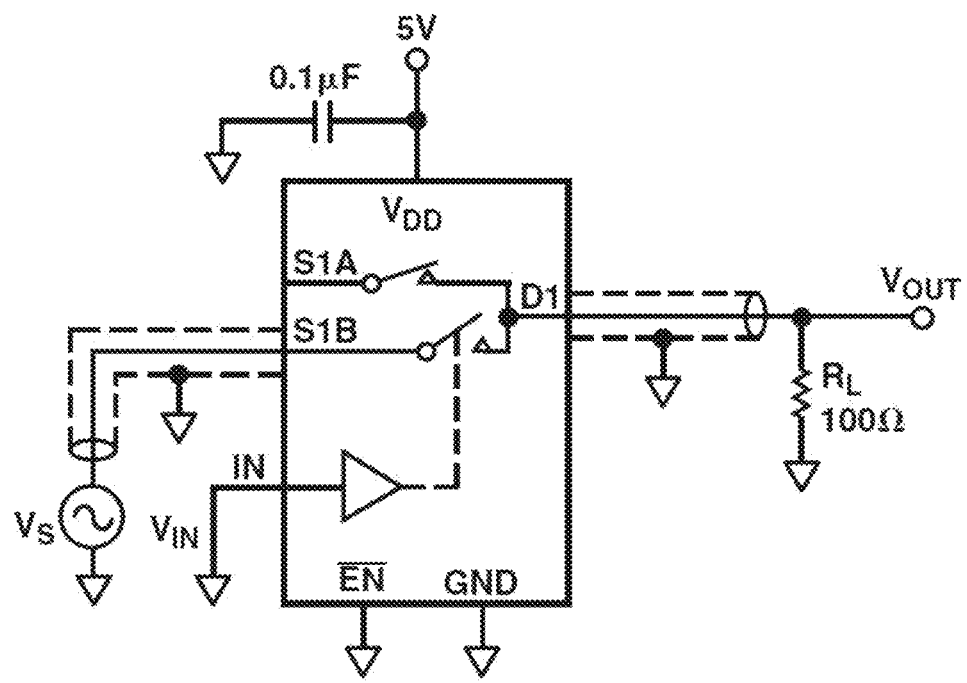
FIG. 8 shows the test circuit for determination of off-isolation.
Figure 9:
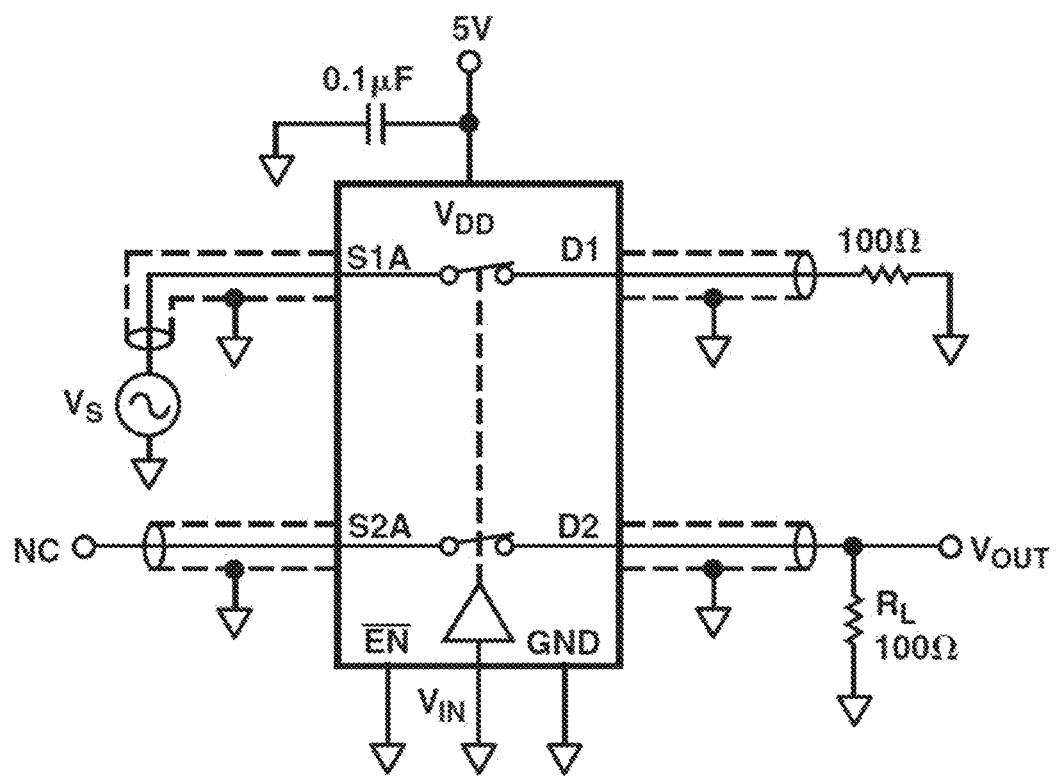
FIG. 9 shows the test circuit for determination of crosstalk isolation.
Figure 10:
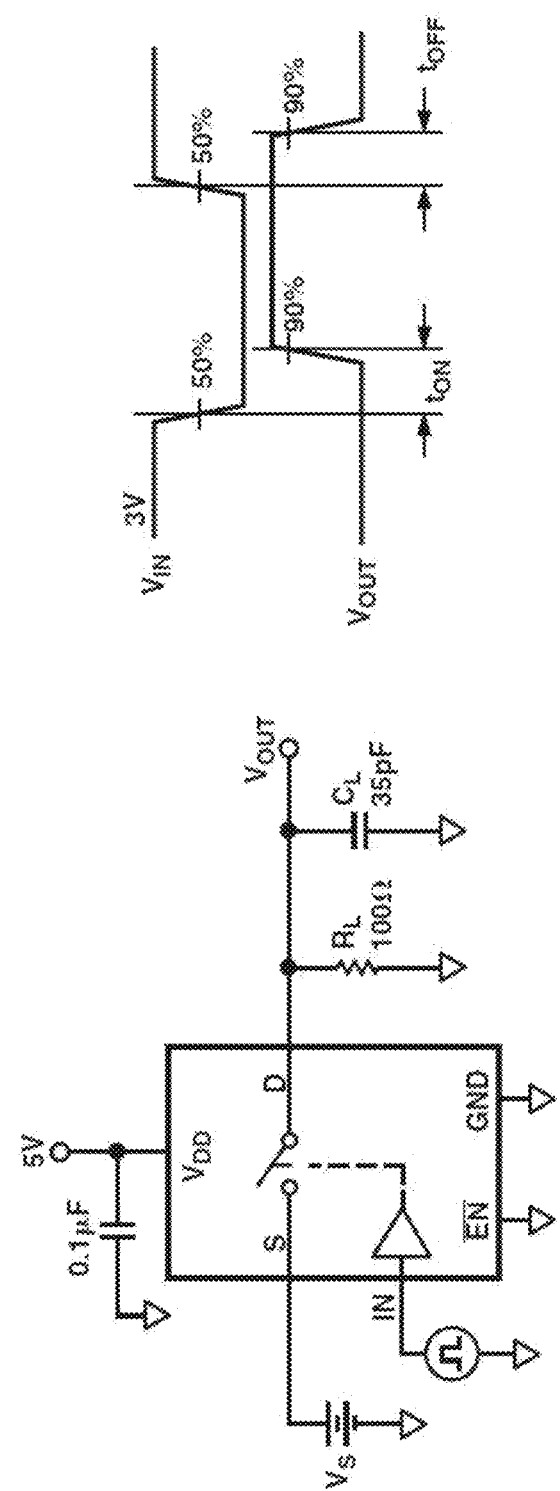
FIG. 10 shows the test circuit for determination of switching times.
Figure 11:
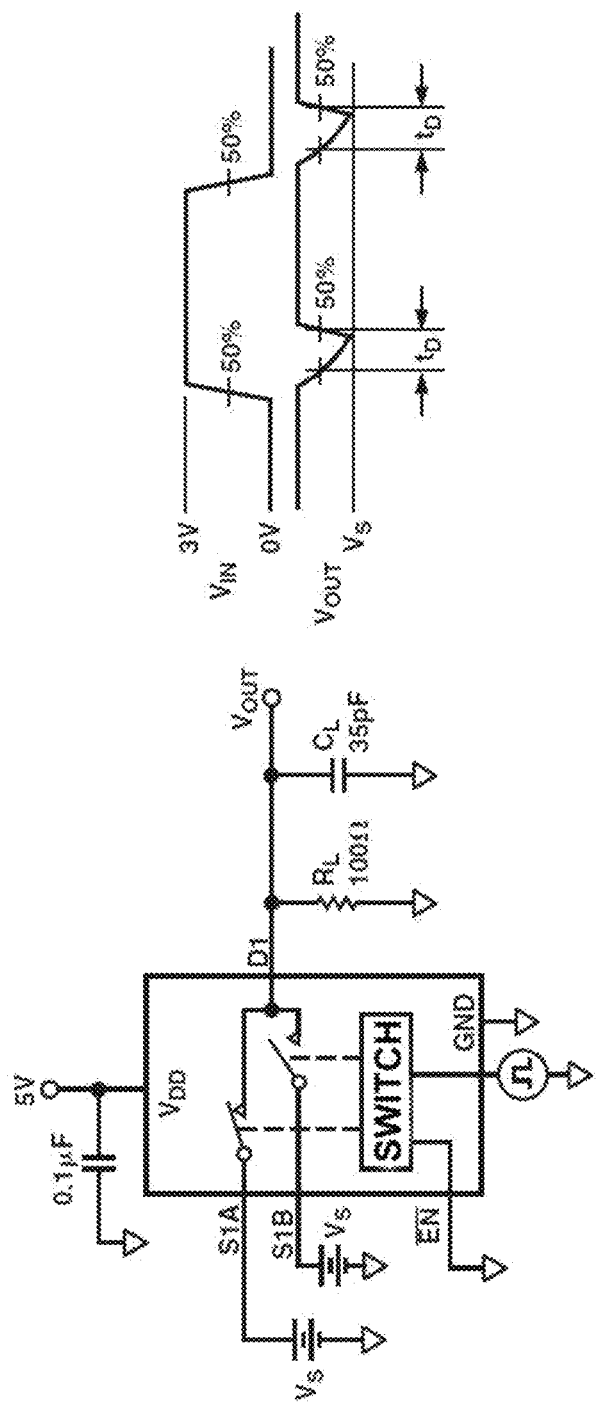
FIG. 11 shows the test circuit for determination of break-before-make time delay.

The improvement of the system as shown in FIG. 6 is based on the fact that the EPR streams are amplified in parallel by the FPR paths, but the final digitalization of the analog streams by the ADC is typically carried out in the form of a multiplexed stream. In consequence, with typically 16 to 64 amplified streams which are multiplexed, there is only $\frac{1}{30}$ to $\frac{1}{60}$ of the time window used for the digitalization of each stream. For example, when EPS streams are sampled with 4 kHz, i.e. 4000 times per second, an acquisition period has a duration of about 250 microseconds (FIG. 6 A). Multiplexing of 30 channels and digitizing with at least 10 MHz means that a single data point is digitized with $\frac{1}{10}$ microseconds whereas each channel is digitized over at least 50 microseconds. Assuming a safety windows including switching times, roughly 25 microseconds from the 250 microsecond time window are used for the EPS digitalization per channel. In consequence, there is a time window of more than 200 microseconds which can be used for impedance spectra recording. Depending on the impedance acquisition parameters (number of frequency points and frequency range) conservative calculation leads to possible impedance spectra acquisition higher than 10 kHz. To further improve spectrum resolution and acquirable frequency range, techniques like multi-sinus excitation is known in high speed and high precision impedance analyzers which are preferably used. In order to assure gapless detection of the EPR streams, impedance data acquisition is limited to the available time range, i.e. 200 microseconds in the above example. This may mean that integration over time to improve signal stability/signal to noise ratio is not possible or restricted. Since the impedance spectra can be acquired 4000 times per second (at a sampling frequency of 4 kHz) a signal quality improvement can be achieved by extending averaging of several hundreds to thousand single measurements per second.

When higher EPS sampling frequencies are required (e.g. for monitoring neuronal network activity) the acquisition window can be shortened. In the case of 20 kHz sampling rate the acquisition window is in the range of 50 microseconds (cf. FIG. 6 B). To assure an appropriate time domain for EIS measurement, a high speed multiplexer is preferably used to obtain an EPR acquisition time shorter than 3 microseconds. Therefore, more than 30 microseconds are available for EIS measurement. Conservatively calculated there is a possibility to acquire impedance values or even spectra in a frequency range greater than 70 kHz.

Thus, using a system according to the present application, which is based on a high speed switchable setup, the acquired data consists of gapless EPR stream as well as impedance values for discrete frequencies or even whole impedance spectra at a frequency range that only depends on the needed EPR sampling frequency (FIG. 6 C).

The invention claimed is:
1. System for monitoring impedance and electric potential of cells in vitro, comprising a) a cell-substrate including at least one electrode for contacting said cells and at least one reference electrode,
b) a device capable of impedance measurement between the electrodes (impedance analyzer),
c) a device for measuring the electric potential difference between the electrodes (potential analyzer) and
d) a switch for selectively connecting the electrodes either to the impedance analyzer or to the potential analyzer, characterized in that the switch has an on-resistance lower than 50 Ohm, an off-isolation of lower than −60 dB, and a crosstalk isolation lower than −60 dB.

2. System according to claim 1, wherein the switch has an on-resistance lower than 10 Ohm.

3. System according to claim 1, wherein the switch has an off-isolation of lower than −75 dB.

4. System according to claim 1, wherein the switch has a crosstalk isolation of lower than −75 dB.

5. System according to claim 1, wherein the cell is an excitable cell, in particular a cardiac cell or neuronal cell.

6. System according to claim 1, wherein the switch is based on a digital signal processor (DSP) or a field programmable gate array (FPGA).

7. System according to claim 1, wherein both the impedance analyzer and the potential analyzer have millisecond time resolution, and the switch is capable of switching the electrodes between the impedance analyzer and the potential analyzer within a time range below 1000 microseconds.

8. System according to claim 1, wherein at least one electrode for contacting said cells is a microelectrode, and wherein the cell-substrate is a microelectrode array.

9. Method for monitoring impedance and electric potential of cells in vitro, comprising the steps of
i) providing a system comprising
a) a cell-substrate including at least one electrode for contacting said cells and at least one reference electrode,
b) a device capable of impedance measurement between the electrodes (impedance analyzer),
c) a device for measuring the electric potential difference between the electrodes (potential analyzer), and
d) a switch for selectively connecting the electrodes either to the impedance analyzer or to the potential analyzer, and
ii) switching the electrodes either to the impedance analyzer or to the potential analyzer for measuring the impedance and the electric potential of the cells, respectively, wherein the switch has an on-resistance lower than 50 Ohm, an off-isolation of lower than −60 dB, and a crosstalk isolation lower than −60 dB.

10. Method according to claim 9, wherein the switch has an on-resistance lower than 10 Ohm.

11. Method according to claim 9, wherein the switch has an off-isolation of lower than −75 dB, and/or a crosstalk isolation of lower than −75 dB.

12. Method according to claim 9, wherein both the impedance analyzer and the potential analyzer have millisecond time resolution, and the electrodes are switched by a switch capable of switching the electrodes between the analyzers with millisecond time resolution between the analyzers in a time range below 1000 microseconds.

13. Method according to claim 12, wherein the switching is conducted such that the impedance is measured between two sampling points of the electric potential measurement.

14. Method according to claim 9, wherein the switch is based on a digital signal processor (DSP) or a field programmable gate array (FPGA).

15. Method according to claim 9, wherein at least one electrode is a microelectrode, and wherein the cell substrate is a microelectrode array.

* * * * *